United States Patent [19]

Djurickovic

[11] 4,331,686
[45] May 25, 1982

[54] TREATMENT OF OTITIS EXTERNA IN DOGS WITH BETA-(1-ADAMANTYL)-ALPHA,ALPHA-DIMETHYLETHYLAMINE

[75] Inventor: Slobodan M. Djurickovic, Middletown, Md.

[73] Assignee: Pennwalt Corporation, Philadelphia, Pa.

[21] Appl. No.: 297,395

[22] Filed: Aug. 28, 1981

[51] Int. Cl.³ ............................................. A61K 31/13
[52] U.S. Cl. .................................................... 424/325
[58] Field of Search ........................................ 424/325

[56] References Cited

U.S. PATENT DOCUMENTS 4,100,170 7/1978 Shetty ................................ 424/325

Primary Examiner—Sam Rosen

[57] ABSTRACT

Otitis Externa is treated in dogs by administering to the infected animal a dosage effective to alleviate the symptoms of the infection of a composition of beta-(1-adamantyl)-alpha,alpha-dimethylethylamine or its acid salt and at least one pharmaceutically acceptable carrier wherein the amine (or its salt) is from about 0.01 to about 95% by weight of the composition.

7 Claims, No Drawings

TREATMENT OF OTITIS EXTERNA IN DOGS WITH BETA-(1-ADAMANTYL)-ALPHA,ALPHA-DIMETHYLETHYLAMINE

BACKGROUND OF THE INVENTION

The invention relates to a method of treating Otitis externa in dogs with a composition of beta-(1-adamantyl)-alpha,alpha-dimethylethylamine or its acid salt, preferably the hydrochloride and at least one pharmaceutically acceptable carrier.

Otitis externa, an inflammation of the external auditory meatus, is a common disease in dogs. Although the disease is not fatal, it is aesthetically disagreeable to the owner and causes discomfort to the affected dogs and may result in internal ear infection and deafness. The microbial flora of the ear canal of dogs suffering from this disease has been studied by several workers, but results of these studies and conclusions differ widely. Although the etiology of Otitis Externa in the dog remains poorly defined, the most frequent microorganisms found in dogs affected with this disease are blastomyces, staphylococci, pytyrosporum canis, pseudomonas, proteus and prototheca wickerhammii. The highest percentage of dogs having this disease tends to be among the breeds of dogs with pendulous ears and long hair; the disease in these dogs sometimes spreads to the neck and head areas that the ears are in constant contact. Adult dogs tend to contract the disease more than others. (see V. D. Sharma and H. E. Rhoads, J. Small Animal Pract., 16, pp. 241 to 247 (1957)).

Prior to the instant invention, treatment of Otitis Externa was based on the prolonged deep instillation of antibiotics, antifungals, corticosteroids, and proteolytic enzymes. In general, many of the dogs treated in this manner did not respond well to the treatment and had to be retreated. Beta-(1-adamantyl)-alpha,alpha-dimethylethylamine has now been found to treat dogs successfully for Otitis Externa.

No prior art is known which discloses the use of beta-(1adamantyl)-alpha,alpha-dimethylethylamine for the treatment of Otitis Externa in dogs.

U.S. Pat. Nos. 3,270,036, 3,489,802, and 3,501,511 teach various adamantylamine and adamantylalkylamine derivatives which have a number of valuable pharmaceutical characteristics such as being used as hypoglycemic agents and antiviral agents.

U.S. Pat. No. 4,100,170 teaches adamantylethylamines that are useful as anorexic agents.

SUMMARY OF THE INVENTION

This invention is directed to a method for treating Otitis Externa in dogs comprising administering to dogs a dosage effective to alleviate the symptoms of the infection of a composition of beta-(1-adamantyl)-alpha,alpha-dimethylethylamine or its acid salt and at least one pharmaceutically acceptable carrier, wherein the amine (or its salt) is from about 0.01 to about 95% by weight of the composition.

The identity of the acid forming the salt of the amine of the composition is not critical. The hydrochloride of the amine is preferred, but any pharmaceutically acceptable inorganic or organic acid such as the sulfate, acetate, nitrate or the like may be used.

DETAILED DESCRIPTION OF THE INVENTION

The drug of this invention can be administered in the microbial and fungal disease treatment according to this invention by any means that effects contact of the active ingredient compound with the site of infection on the dog. For example, a dosage form of the drug may be used for oral, parenteral, topical, aural, or rectal application. The dosage form may be a solution, gel, emulsion, suspension, paste, ointment, suppository, tablet, capsule, powder, granule or an aerosol product or other suitable formulation. The dosage administered will be dependent upon the weight of the dog and the frequency of the required treatment. Generally, a daily topical dosage of active ingredient will be from about 1 to 50 milligrams per kilogram of the dog's body weight, although lower and higher amounts can be used. The active ingredient, the drug, can be employed in useful compositions according to the present invention in such dosage forms as solution, semisolid, solid, and aerosol forms. These dosage forms preferably deliver from about 1 mg to about 500 mg of active ingredient, with the range from about 10 mg to about 200 mg being most preferred. In these dosage forms the composition will contain at least one non-toxic pharmaceutically acceptable carrier for the active ingredient. Examples of the non-toxic carriers or adjuvants are viscosity enhancers such as bentonite, celluloses (e.g., methylcellulose, ethylcellulose, and carboxy methylcellulose) and tragacanth; pH modifiers such as dibasic sodium phosphate, citric acid, and sodium hydroxide; preservatives such as methyl paraben, propyl paraben, benzoic acid, and benzyl alcohol; sweeteners such as saccharin, sorbitol (D-glucitol), and mannitol; stability enhancers such as sodium bisulfite and ascorbic acid; coloring agents such as food, drug and cosmetic (FD&C) and drug and cosmetic (D&C) colors certified by the Food and Drug Administration (FDA); solvents such as water, alcohol (e.g., ethyl alcohol (for internal use) and isopropyl alcohol (for external use)), and propylene glycol; suspending agents such as kaolin, celluloses (e.g. methylcellulose, ethylcellulose and carboxy methylcellulose), acacia, and tragacanth; granulating agents such as acacia, sucrose, and polyvinylpyrrolidone (PVP); coating agents such as celluloses (e.g., ethylcellulose and propylcellulose) and PVP; disintegration/dissolution modifiers such as starch (e.g., corn starch, rice starch and potato starch) and polysorbate 80 (polyoxyethylene (20) sorbitan monooleate); excipients such as lactose, starch, and cellulose; propellents such as isobutane, fluorocarbon 11 (trichlorofluoro methane), fluorocarbon 12 (dichlorodifluoro methane), and ion exchange agents such as XE-69 and IR 120 (sulfonic acid cation resins (styrene divinyl benzene)) and IRP 58 (a phenolic polyamine anion exchange resin); emulsifying agents such as glyceryl stearate (self emulsifying), sorbitan stearate, decyl oleate, cetearyl alcohol, polysorbate 60 and triethanolamine; and humectants such as myristyl myristate.

Typical embodiments of the pharmaceutical composition of this invention are: (all percentages are by weight of composition)

1. Tablet:

| | |
|---|---|
| drug | 100 mg |
| microcrystalline cellulose | 100 mg |

-continued

| | |
|---|---|
| magnesium stearate | 5 mg |
| 2. Capsule: | |
| drug | 100 mg |
| lactose | 100 mg |
| starch | 5 mg |
| magnesium stearate | 2 mg |
| 3. Oral Solution: | |
| drug | 2 g |
| sorbitol (D-glucitol) solution 70% | 50 ml |
| citrus flavor | 1 g |
| citric acid | 1 g |
| distilled water, quantity sufficient to make (q.s. ad) | 100 ml |
| 4. Parenteral Solution: | |
| drug | 2.5 g |
| benzyl alcohol | 0.1 g |
| sterile distilled water, q.s. ad | 100 ml |
| 5. Aerosol Spray: | |
| drug | 5% |
| polysorbate 20 (polyoxyethylene 20 sorbitan monolaurate) | 0.1% |
| propellent 11/12, 40/60 ratio by weight, q.s. ad | 100% |
| 6. Topical Lotion: | |
| drug | 5% |
| mineral oil | 30% |
| polysorbate 80 | 10% |
| propylene glycol | 5% |
| white petrolatum | 5% |
| benzoic acid | 2% |
| perfume | 0.1% |
| water q.s. ad | 100% |
| 7. Topical Ointment: | |
| drug | 5% |
| hydrophilic ointment U.S.P. q.s. ad | 100% |
| 8. Oral Resinated Suspension (sustained release): | |
| drug resinate | 10% |
| (drug content of resin is | 15%) |
| keltrol (xanthan gum) | 10% |
| saccharin | 0.5% |
| flavor | 0.2% |
| sorbitol 70% solution | 50% |
| methylparaben | 0.5% |
| water, q.s. ad | 100% |
| 9. Oral Resinated Capsule (sustained release): | |
| drug resinate | 200 mg |
| (drug content of resin is | 50%) |
| lactose 100 mg | |
| magnesium stearate | 5 mg |
| 10. Topical Gel: | |
| drug | 5% |
| carbopol 934 (carboxypolymethylene) | 1% |
| alcohol | 10% |
| triethanolamine | 0.8% |
| polyethylene glycol 300 | |
| water q.s. ad | 100% |

Note that "drug" in each of the above examples is beta-(1-adamantyl)-alpha,alpha-dimethylethylamine or its acid salt.

EXAMPLE

Beta-(1-Adamantyl)-alpha,alpha-dimethylethylamine hydrochloride (I) was tested for its antimicrobial and antifungal activity against Otitis Externa in dogs using the following method. Dogs A and B, which were diagnosed to have Otitis Externa, had their ears washed with Ivory soap and were treated with a 4% aqueous solution of (I) once a day; the drug was applied topically to the affected ears in the following aqueous solution:

| | |
|---|---|
| Compound (I) | 4 g/100 ml as base |
| Isopropyl alcohol | 32 ml/100 ml |
| Polyethylene glycol 200 | 8 ml/100 ml |
| D.I. water q.s. ad | 100 ml. |

Within three days both dogs showed noticeable improvement. The redness in the ears disappeared, and the ulcerations began to heal. The ears appeared generally dryer, and the erythema and edema disappeared.

After eight days of treatment, dog A had almost completely recovered. His ears were just slightly red, and each ear had one small abscess but the rest of the lesions and ulcerations had completely healed; the hair on the ears had started to grow back. By the sixteenth day, dog A was completely healed and all his hair had grown in. Dog A was examined every day for a further month and did not show any signs of recurrence of the disease.

After eight days of treatment, dog B had also almost completely recovered; the swelling in the ears had disappeared and most of the open ulcerations had healed while the few ulcerations that remained were dry and in the last stages of healing. The ruffled edges of the ear flopes were disappearing also. The application of the 4% solution to the dog's ears was stopped after 22 days. On the fourteenth day, however, it was observed that dog B also had similar lesions on his neck. Hence, dog B's neck was clipped, washed with Ivory soap, and then treated with the above-mentioned 4% aqueous solution of compound (I), which was applied topically to the affected neck for 17 days. The neck lesions completely disappeared. Dog B was examined for an additional two weeks with no signs of the disease recurring.

What is claimed is:

1. A method for treating Otitis Externa in dogs comprising administering to dogs, a dosage effective to alleviate the symptoms of the infection, a composition of beta-(1-adamantyl)-alpha,alpha-dimethylethylamine or its acid salt and at least one pharmaceutically acceptable carrier, wherein the amine is from about 0.01 to about 95% by weight of the composition.

2. The method of claim 1 wherein the composition is administered to the dogs by physically applying the composition to the affected areas.

3. The method of claim 2 wherein the composition is applied to the affected areas in the form of an aqueous solution.

4. The method of claim 3 wherein the pharmaceutically accepted carriers are isopropyl alcohol and polyethylene glycol 200.

5. The method of claim 2 wherein the composition applied to the affected areas is in the form of an ointment.

6. The method of claim 2 wherein the composition applied to the affected areas is in the form of a cream.

7. The method of claim 1 wherein the composition is beta-(1-adamantyl)-alpha,alpha-dimethylethylamine hydrochloride.

* * * * *